United States Patent [19]

Scott

[11] Patent Number: 4,723,942

[45] Date of Patent: * Feb. 9, 1988

[54] CLINICAL CATHETERIZATION TECHNIQUE AND APPARATUS FOR PERFORMING SAME

[76] Inventor: Van E. Scott, 31220 Wedgewood Dr., No. 201, Walled Lake, Mich. 48088

[*] Notice: The portion of the term of this patent subsequent to Oct. 28, 2003 has been disclaimed.

[21] Appl. No.: 890,083

[22] Filed: Jul. 24, 1986

Related U.S. Application Data

[63] Continuation of Ser. No. 647,930, Sep. 6, 1984.

[51] Int. Cl.4 .............................................. H61M 5/00
[52] U.S. Cl. .................................... 604/164; 128/658
[58] Field of Search ........................ 604/53, 164-170, 604/280-284; 128/656-658, 772

[56] References Cited

U.S. PATENT DOCUMENTS

| 3,547,103 | 12/1970 | Cook | 604/170 X |
|---|---|---|---|
| 3,570,485 | 3/1971 | Reilly | 604/53 |
| 3,742,958 | 6/1973 | Rundles | 604/164 |
| 3,921,631 | 11/1975 | Thompson | 604/160 |
| 4,306,562 | 12/1981 | Osborne | 604/164 X |
| 4,405,314 | 9/1983 | Cope | 604/164 X |
| 4,412,832 | 11/1983 | Kling et al. | 604/161 |
| 4,451,256 | 5/1984 | Weikl et al. | 604/164 |
| 4,464,171 | 8/1984 | Garwin | 604/53 |
| 4,498,902 | 2/1985 | Ash et al. | 604/164 |

OTHER PUBLICATIONS

Seldinger, S. I. "Catheter Replacement of the Needle in Percutaneous.

Primary Examiner—Dalton L. Truluck
Attorney, Agent, or Firm—Cullen, Sloman, Cantor, Grauer, Scott & Rutherford

[57] ABSTRACT

An improved clinical technique for central venous catheterization and apparatus for performing same. The catheterization apparatus includes a small gauge hollow steel needle having a long plastic catheter introducer covering all but the very tip of the needle. The needle positions the plastic introducer into the vein whereupon the needle is removed. Next, a guide wire is inserted into the introducer and into the vein. After the guide wire is in place, the introducer is peeled away from the guide wire, and the guide wire and plastic catheter are threaded into the central venous system. Once the catheter is in place, the guide wire is removed, the catheter is attached to an intravenous unit and the catheter is sutured to the skin.

2 Claims, 6 Drawing Figures

CLINICAL CATHETERIZATION TECHNIQUE AND APPARATUS FOR PERFORMING SAME

This application is a continuation of my U.S. patent application, Ser. No. 647,930, filed Sept. 6, 1984.

FIELD AND BACKGROUND OF THE INVENTION

The present invention relates generally to an improved clinical technique for catheterization and apparatus for performing same, and more particularly, an improved technique for central venous catheterization.

The sole objective of central venous catheterization is to establish a direct conduit from the exterior of the body to the superior vena cava. Thus, catheterization of the superior cava is invaluable in special circumstances when there is critical necessity to: (1) measure central venous pressure frequently to guide fluid balance endeavors in persons with marginal cardiac or renal reserve; (2) procure aliquots of mixed venous blood repeatedly for gasometric or biochemical analysis; (3) administer massive volumes of fluids or blood rapidly for resuscitation and ancillary purposes; and (4) infuse intravenously, over long periods of time, hypertonic, acidic, or kindred irritant solutions which would assuredly incite phlebosclerosis were they not diluted right away in the faster stream of central venous channels.

Traditionally, central venous catheterization has been saved as a last resort when other routes were non-existent at the outset or became exhausted. It has been considered preferable to try a safer procedure before using one that carried risks. However, the benefits of using a central insertion site may outweigh the risk because the central venous vein: (1) is closer to the cava; (2) has a constant location; (3) is relatively big; (4) has a fairly large volume flow through it; (5) is less liable to collapse or go into spasm, being kept patulous by fibrous attachments from its walls to adjacent rigid structures; (6) rarely is anomalous or diseased; and (7) is sheltered by the clavicle from ordinary external trauma.

Several techniqes have been developed in the past in an attempt to reduce the risks associated with central venous catheterization. One such attempt is the "through the needle" technique for catheterization whereby the patient is first placed in the trendelenburg position (supine with feed higher than head). Then, the skin over and around the subclavian vein is cleaned with antiseptic solution and a sterile field or working area is set-up using sterile towels. A small area of skin (the proposed puncture site) within the sterile field is then anesthetized by injecting a small amount of local anesthetic into the skin using a small hollow needle and syringe. Next, a large (14 gauge 7 cm long) hollow needle with a syringe is passed through the anesthetized skin and into the vein. After puncturing the skin, continuous suction is applied to the syringe. By applying continuous suction, entrance into the subclavian vein is signaled by the appearance of blood into the attached syringe. Once the needle is in position, the syringe is removed from the needle and a smaller diameter catheter (16 gauge flexible hollow tube about 50 cm long) is passed through the needle along the course of the vein and into the central venous system (superior vena cava). The needle is then withdrawn over the catheter, leaving the catheter in the puncture site.

There are several distinct disadvantages associated with the utilization of the through the needle catheterization technique. First, because a large needle must be used, there is an increased chance of pneumothorax if the pleura cavity is punctured and a greater chance of air embolus when the syringe is removed from the needle to insert the catheter. In addition, because the needle is larger than the catheter, the puncture wound is not sealed completely by the catheter, increasing the chance of the ingress of air (air embolus) and seepage of blood (hematoma formation) around the catheter. Furthermore, the larger needle the greater the chance of hemorrhage if the subclavian artery is punctured. Because the catheter must pass over the sharp edge of the needle, the tip of the catheter may be seared off into the blood stream causing embolus. Lastly, because the catheter is flexible, it is hard to direct it into the right position during insertion and my have a tendency to buckle or kink when it meets resistance, especially when turning corners. Thus, there has been a need for an improved catheterization technique and apparatus for performing same which overcomes these disadvantages while providing an improved technique as compared to prior conventional techniques.

Alternatively, it is conventional to use an "over the wire" catheterization technique. As with the through the needle catheterization technique, the patient is prepared as set forth above. However, a larger (16 gauge 7 cm long) hollow needle with a syringe attached is passed through the anesthetized skin and into the subclavian vein. After puncturing the skin, continuous suction is applied to the syringe the appearance of blood signals entrance into the vein. Next, the syringe is taken off the needle and a long 70 cm guide wire, with a floppy tip and a diameter about equal to the internal diameter of the needle, is passed through the needle, floppy end first, into the vein. The needle is then withdrawn from the patient over the guide wire and a long 50 cm 16 gauge hollow catheter is threaded onto the wire. Next, the wire and the catheter are passed along the inside of the subclavian vein into the central venous system (superior vena cava).

There is a distinct disadvantage associated with the utilization of the above mentioned over the wire catheterization technique, namely that the technique is substantially slower than the through the needle technique. First, the guide wire must be threaded through the needle into the subclavian vein and then the needle removed. Next, the catheter must be threaded onto the wire, and then both are threaded inside of the vein into the central venous system. Finally, after all of the above, the wire is removed. All these steps require substantial time, which may be unavailable and time is of vital importance in an emerency situation. Thus, there has been a need for an improved catheterization technique which overcomes these disadvantages while providing an improved technique as compared to prior techniques.

The present invention is directed to an improved clinical catheterization technique and apparatus for performing same which is superior to conventional methods of central venous catheterization and which offers a combination of quick application, better control of catheter positioning and decreased chances of air embolus, hemorrhage, hematoma formation, catheter embolus and pheumothorax.

SUMMARY OF THE INVENTION

The present invention provides an improved clinical technique and apparatus for catheterization. Specifically, according to the principles of the present invention the patient is prepared using conventional techniques. Namely, the patient is first placed in the trendelenburg position (supine with feet higher than head). Next, the skin over and around the subclavian vein is cleaned with antiseptic solution, and a sterile field of working area is set-up using sterile towels. A small area of the skin (the proposed puncture site) is then anesthetized by injecting a small amount of local anesthetic into the skin using a small hollow needle and syringe. According to the principles of the present invention, after preparing the patient and the proposed puncture site, a small steel needle is passed through the anesthetized skin and into the subclavin vein. A small flexible, tubular catheter introducer, slit lengthwise from tip through base, covers all but the exposed tip of the steel needle. After puncturing the skin, continuous suction is applied to a syringe attached to the steel needle. Entrance into the vein is signaled by the appearance of blood in the syringe. The small introducer is then pushed further into the vein and the needle is removed. An exposed floppy tip of a guide wire with a plastic catheter attached to its other end, is then passed through the small catheter introducer so that the tip of the guide wire is in the vein. Then, the small previously slit introducer is pulled out of the vein and skin. The introducer is then peeled away from the guide wire, through the slit. The exposed portion of the guide wire and plastic catheter assembly are then threaded into the central venous system. After properly positioning the plastic catheter and guide wire, the guide wire is removed through the catheter and the catheter is attached to an intravenous set and sutured to the skin.

The improved catheterization technique provides several advantages over conventional techniques and reduces several of the risks associated therewith. Specifically, the improved technique and apparatus allows for the positioning of the catheter more easily and quickly. The small needle decreases the chance of pneumothorax if the pleura is punctured and decreases the chances of air embolus when the syringe is removed to insert the guide wire. In addition, the smaller needle decreases the change of hemorrhage if the artery is puncture. Further, because the puncture site more closely matches the catheter, a better seal is provided when the catheter is placed in position to decrease the chance of the ingress of air or air embolus, and the seepage of blood or the formation of hematoma are decreased.

The improved clinical catheterization technique and apparatus for performing same provides an improved means for the infusion of fluids into circulatory system following trauma, pathological fluid loss, or the like, that is uncomplicated and inexpensive to manufacture and use.

DESCRIPTION OF THE DRAWINGS

Various objects, benefits, and advantages of the present invention will become more apparent upon reading the following detailed description in conjunction with the drawings where like reference numerals identify corresponding components.

DETAIL DESCRIPTION OF A PREFERRED EMBODIMENT

Figure 1:
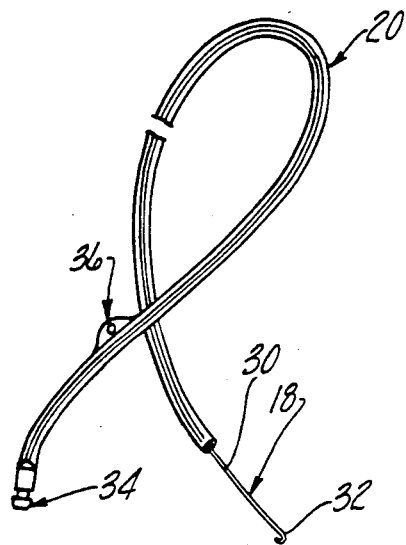
FIG. 1 is a side view of the central venous catheterization apparatus of the present invention showing the guide wire and catheter of the present invention.
Figure 2:
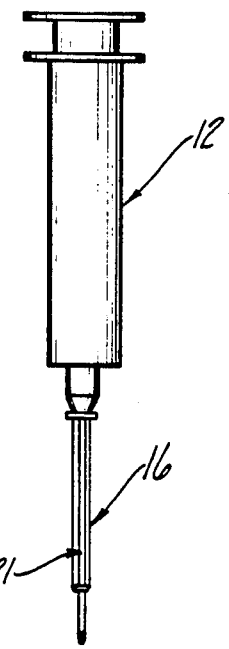
FIG. 2 is a side view of the needle, syringe and introducer of the present invention.

Referring to FIGS. 1 and 2 of the drawings, the improved clinical catheterization technique and apparatus for central venous catheterization is illustrated. The catheterization apparatus includes a syringe 12, hollow needle 14, plastic sheath or catheter introducer 16, guide wire 18, and catheter 20.

Figure 3:
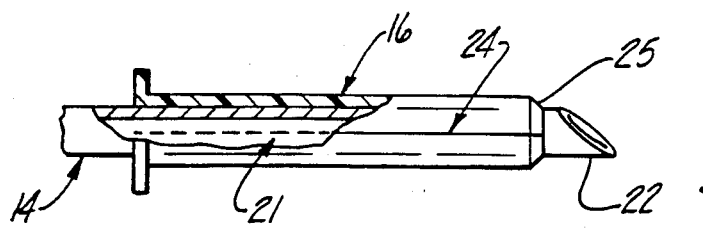
FIG. 3 is an enlarged side view, partially cross-sectioned, of the needle and introducer.

Referring now to FIGS. 2 and 3, hollow needle 14 is attached to syringe 12, and sheath or flexible tubular introducer 16 covers shaft portion 21 of needle 14 to adjacent tip 22. A slit 24 extends longitudinally the entire length of introducer 16 parallel to the central axis of needle 14. Introducer 16 has a frustoconical end portion 25. The particular material of which needle 14 is made is not essential to the present invention. The needle is a trocar to pierce and transverse tissue before penetrating the vein with its tip which is sharp and slanted. A suitable material is 16 to 20 gauge steel tubing which provides rigidity and easy sterilization.

Referring again to FIG. 1, guide wire 18 and plastic catheter 20 may be telescopically receivable and may be attached whereby exposed portion 30 of guide wire 18 partially extends from catheter 20. Guide wire 18 may fit snugly into catheter 20 or may be accommodated by a dialator (not shown). Guide wire 18 has an exposed floppy tip or J-shaped tip 32 to held end 32 of guide wire 18 to remain central while being inserted into the central venous system, instead of catching in the venous walls and puncturing the vein, or curling. Therefore, the soft-tip wires are good for use in almost all veins and almost all circumstances. However, running a stiff tip through needle 14 into the vein can be dangerous because it can penetrate through the vein into the underlaying structure.

In the illustrated embodiment, for central venous subclavian catheterization, exposed potion 30 of guide wire 18 is approximately 20 cm in length with guide wire 18 having a total length of approximately 70 cm. Portion 30 is capable of passing through a plastic sheath or catheter introducer 16 for positioning catheter 20 within the subclavin vein. In addition, catheter 20 is approximately 50 cm long of 16 gauge plastic tubing. Because catheter 20 has to negotiate curvatures on its way and float freely without hurting the vein lining, it should be flexible and smooth tipped. For example, catheter 20 and introducer 16 may be constructed of a tubular material such as silicone elastomer, teflon, polyethylene or the like. The softer and more pliable the tubing the more likely it will glance off the vein wall without perforating the later.

As is disclosed, a knob 34 is fixably attached to guide wire 36 for easy removal upon properly positioning catheter 20 within the subclavian vein.

Clinical Method and Use

Figure 4:
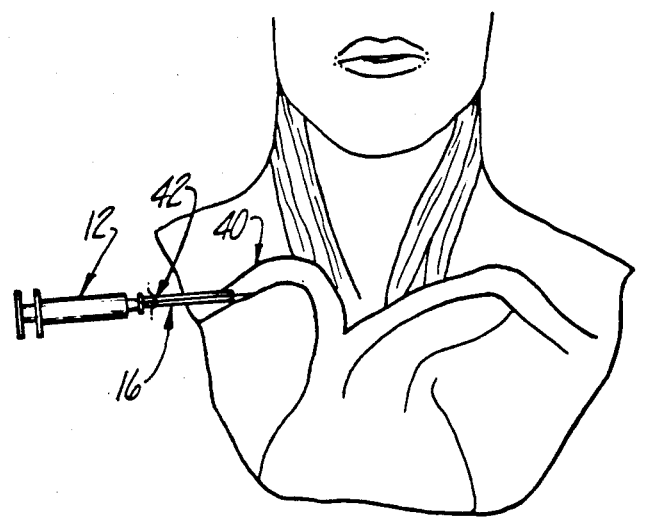
FIG. 4 is a schematic side view of a patient showing insertion of the needle and introducer into the puncture site and subclavian vein.

The operation and use of the present improved catheterization technique may now be explained. The patient is first placed in the trendelenburg position (supine with feet above the level of the head) in a manner well known in the medical art, by laying the patient flat on his back, unpropped on bolsters, shoulders relaxed and neither hunched nor shrugged. The upper half of the patient's body should be tilted down 15 to 30 degrees from the horizontal, arms straight alongside the trunk or hands crossed over the abdomen, and the face turned slightly away from the operating site. Next, the skin over and around the subclavian vein 40 is cleansed with an antiseptic solution. A sterile field or working area is then setup using sterile towels. A small area of skin at the proposed puncture site 42 is then anesthetized by injecting a small amount of local anesthetic into the skin. As shown in FIG. 4, needle 14 and introducer 16 are both passed through the anesthetized skin 42 and into the subclavian vein 40.

After puncturing the skin, continuous suction is applied to syringe 12 attached to needle 14. It is very important that the user aspirate continuously as he advances needle 14 so that entrance into the subclavian vein 12 is signaled by the appearance of blood in the syringe. Many times blood will not flash back unless a syringe is attached to the needle because pressure in the vein is low. In addition, it is very easy to go all the way through the vein without realizing it, especially if needle 14 is inserted during inspiration, when the vein may be more collapsed. The plastic sheath or introducer 16 is then pushed further into the subclavian vein 40 and syringe 12 and needle 14 are removed.

Figure 5:
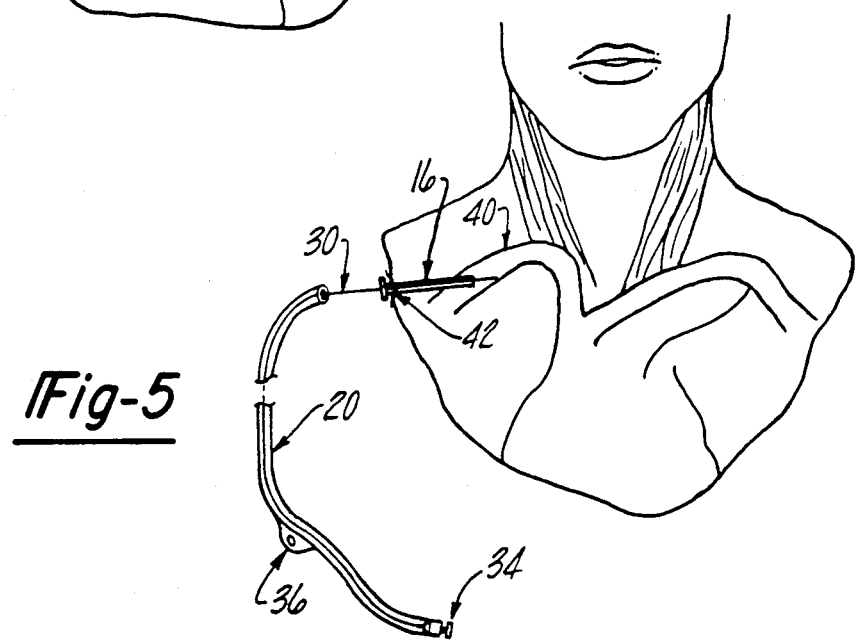
FIG. 5 is a schematic side view of a patient similar to FIG. 4 showing the insertion of the guide wire.
Figure 6:
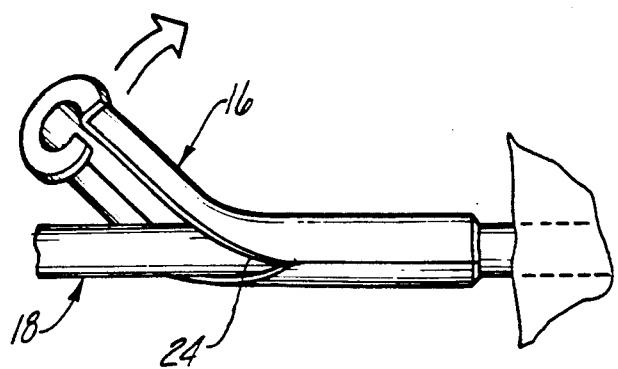
FIG. 6 is a side view of the introducer of the present invention being peeled away from the guide wire.

As illustrated in FIG. 5, the exposed floppy tip 32 of guide wire 18 is then threaded into introducer 16 so that the tip of the guide wire is in the subclavian vein. It is imperative that guide wire 18 not be forced, but it should literally "float" right in. Then, introducer 16 is pulled out of the subclavian vein and skin 42 along the exposed portion of guide wire 18. Next introducer 16 is peeled away from the guide wire through slit 24, FIG. 6. The slit makes this maneuver possible. Catheter 20 and guide wire 18 are then threaded into the central venous system. The catheter will be forced to follow along the route of the guide wire and therefore go into the vein. Next, after properly positioning catheter 20, guide wire 18 is removed by pulling on knob 34 which is attached to guide wire 18.

After the guide wire is removed, catheter 20 can then be attached to an intravenous apparatus and sutured to the skin in a manner well known in the art. For example, the catheter may be anchored to the skin by 3-point fixation with non-absorbable suture. Stiches may warp or brake plastic catheter 20, so strips of sterile paper adhesive tape or catheter guard may be wrapped around the section of the catheter to be tied. Alternatively, catheter 20 may be sutured to the patient's skin by tab 36.

The present catheterization technique described can be used with any of the current methods and techniques of central venous catheterization such as femoral vein, internal jugular vein, external jugular vein, supraclavicular subclavian vein and surgical cut down. Perecutaneous subclavian central venous catheterization means to pass a hollow flexible tube such as catheter 20 through the skin, under the clavicle, into and then along the inside of the subclavian vein into the central venous system. This is invaluable in special circumstances when there is a critical necessity to: (1) measure central venous pressure frequently to guide fluid balance endeavors in persons with marginal cardiac or renal reserves; (2) procure aliquots of mixed venous blood repeatedly for gasometric or biochemical analysis; (3) administer massive volumes of fluid or blood rapidly for resuscitation and ancilary purposes; (4) infuse intravenously, over long periods of time, hypertonic, acidic or kindred irritant solutions which would assuredly incite phlebosclerosis were they not diluted right away in the faster stream of the central venous channels. Hyperalimentation or total parenteral nutrition formulas are foremost in this catagory. One or more of those specifications appertain to myriad clinical entities: hypovolemic shock, dehydration, cerebral edema; inanition; major trauma; serve hemorrhage; extensive bowel resection; gastrointestinal fistulas; certain cancers requiring prolonged infusion of cytotoxic agents; continuous injection of antibiotics in concentrated doses for treating infective endocarditis; and so forth.

While a preferred embodiment of the present invention has been described so as to enable one skilled in the art to practice the technique of the present invention, the preceding description is intended to be exemplary and should not be used to limit the scope of the invention. The scope of the invention should determined only be reference to the following claims.

What is claimed is:

1. A kit for use in conjunction with a hypodermic syringe for catheterizing a subject, said syringe having a needle with a tip portion for insertion into said subject, said kit comprising:

a substantially cylindrical introducer means having a frustconical first end and a generally planar opposite end and a bore extending through said introducer, said bore having a diameter substantially equal to the outer diameter of said needle such that the introducer tightly engages said needle to create sealing engagement therebetween, and a slit extending the length of said introducer, said introducer being resilient such that the opposed walls of said slit are normally biased against one another to prevent the ingress of fluid into said bore, said introducer being removably positioned about said needle to expose said tip whereby said needle and introducer are easily insertable into said subject and said needle is longitudinally removable from said introducer after insertion;

a guide wire for insertion into said introducer to a desired location within said subject, said introducer being removable from said wire along said slit; and a catheter having an outer diameter generally equal to or greater than the outer diameter of said introducer, said catheter being received by said wire and threadable along said wire into said subject after said introducer has been removed from said wire along said slit;

said bore of said introducer being substantially smaller than the outer diameter of said catheter with said catheter being incapable of entering said bore;

said wire being removable from said catheter when said catheter reaches said desired location.

2. The kit of claim 1, wherein said wire is initially positioned in said catheter prior to passing said wire through said introducer.

* * * * *